United States Patent
Wiemker et al.

(10) Patent No.: US 11,350,897 B2
(45) Date of Patent: Jun. 7, 2022

(54) APPARATUS FOR PRESENTATION OF DARK FIELD X-RAY IMAGE INFORMATION

(71) Applicant: KONINKLIJKE PHILIPS N.V., Eindhoven (NL)

(72) Inventors: Rafael Wiemker, Kisdorf (DE); Andriy Yaroshenko, Garching (DE); Karsten Rindt, Hamburg (DE); Jörg Sabczynski, Norderstedt (DE); Thomas Koehler, Norderstedt (DE); Hanns-Ingo Maack, Norderstedt (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 184 days.

(21) Appl. No.: 16/769,483

(22) PCT Filed: Nov. 22, 2018

(86) PCT No.: PCT/EP2018/082147
§ 371 (c)(1),
(2) Date: Jun. 3, 2020

(87) PCT Pub. No.: WO2019/110313
PCT Pub. Date: Jun. 13, 2019

(65) Prior Publication Data
US 2020/0383652 A1 Dec. 10, 2020

(30) Foreign Application Priority Data
Dec. 7, 2017 (EP) .................................... 17205886

(51) Int. Cl.
*A61B 6/00* (2006.01)
*G06T 5/50* (2006.01)
(Continued)

(52) U.S. Cl.
CPC .............. *A61B 6/484* (2013.01); *A61B 6/466* (2013.01); *A61B 6/50* (2013.01); *A61B 6/5205* (2013.01);
(Continued)

(58) Field of Classification Search
CPC ........... A61B 6/484; A61B 6/466; A61B 6/50; A61B 6/5205; A61B 6/5217;
(Continued)

(56) References Cited

U.S. PATENT DOCUMENTS 7,983,381 B2 * 7/2011 David .................... A61B 6/032
378/4
8,041,004 B2 * 10/2011 David .................... A61B 6/484
378/36
(Continued)

FOREIGN PATENT DOCUMENTS

WO WO2006116700 A2 11/2006
WO WO2009150565 A1 12/2009
(Continued)

OTHER PUBLICATIONS

PCT International Search Report, International application No. PCT/EP2018/082147, dated Feb. 22, 2019.
(Continued)

*Primary Examiner* — Vu Le
*Assistant Examiner* — Julius Chai
(74) *Attorney, Agent, or Firm* — Larry Liberchuk (57) ABSTRACT

The present invention relates to an apparatus (10) for presentation of dark field information. It is described to provide (210) an X-ray attenuation image of a region of interest of an object. A dark field X-ray image of the region of interest of the object is also provided (220). A plurality of sub-regions of the region of interest are defined (230) based on the X-ray attenuation image of the region of interest or
(Continued)

based on the dark field X-ray image of the region of interest. At least one quantitative value is derived (240) for each of the plurality of sub-regions, wherein the at least one quantitative value for a sub-region comprises data derived from the X-ray attenuation image of the sub-region and data derived from the dark field X-ray image of the sub-region. A plurality of figures of merit are assigned (250) to the plurality of sub-regions, wherein a figure of merit for a sub-region is based on the at least one quantitative value for the sub-region. Data representative of the region of interest is output (260) with figures of merit for the respective sub-regions.

13 Claims, 4 Drawing Sheets

(51) Int. Cl.
*G06T 7/00* (2017.01)
*G06V 10/25* (2022.01)

(52) U.S. Cl.
CPC .............. *A61B 6/5217* (2013.01); *G06T 5/50* (2013.01); *G06T 7/0012* (2013.01); *G06V 10/25* (2022.01); *G06T 2207/10116* (2013.01); *G06T 2207/20221* (2013.01); *G06T 2207/30061* (2013.01)

(58) Field of Classification Search
CPC ....... G06K 9/3233; G06T 5/50; G06T 7/0012; G06T 2207/10116; G06T 2207/20221; G06T 2207/30061; G06V 10/25
See application file for complete search history.

(56) References Cited

U.S. PATENT DOCUMENTS

| | | | | |
|---|---|---|---|---|
| 8,515,002 B2* | 8/2013 | Huang | .................. | B82Y 10/00 |
| | | | | 378/6 |
| 8,972,191 B2* | 3/2015 | Stampanoni | ......... | G01N 23/041 |
| | | | | 702/1 |
| 9,001,967 B2* | 4/2015 | Baturin | .................. | A61B 6/482 |
| | | | | 378/71 |
| 9,117,296 B2 | 8/2015 | Stampanoni | | |
| 9,237,877 B2 | 1/2016 | Noji | | |
| 9,439,615 B2 | 9/2016 | Stampanoni | | |
| 9,510,799 B2 | 12/2016 | Makifuchi | | |
| 9,805,467 B2 | 10/2017 | Maack | | |
| 2016/0210739 A1 | 7/2016 | Maack | | |
| 2017/0146466 A1* | 5/2017 | Stutman | ............... | A61B 6/4291 |
| 2018/0271645 A1* | 9/2018 | Brady | .................. | B29D 11/026 |

FOREIGN PATENT DOCUMENTS

| | | |
|---|---|---|
| WO | WO2016177588 A1 | 11/2016 |
| WO | WO2017055527 A1 | 4/2017 |
| WO | WO2018114553 A1 | 6/2018 |
| WO | WO2018192909 A1 | 10/2018 |

OTHER PUBLICATIONS

Yaroshenko, Andre, et al. "Grating-Based X-Ray Dark-Field Imaging: A New Paradigm in Radiography." Current Radiology Reports 2.7, May 23, 2014.

Kelbach K. et al., "Impact of Aspiration on Dark-Field Signal Intensities in Chest Radiographs of Living Pigs", Oral presentation at the European Congress of Radiology, Mar. 1-5, 2017, Vienna, ECR Online 2017, B-03.

Scherer K. et al., "X-Ray Dark-Field Radiography—In-Vivo Diagnosis of Lung Cancer in Mice", Scientific Reports, 7:402, pp. 1-9, 2017.

Pfeiffer F. et al., "Hard-X-Ray Dark-Field Imaging Using a Grating Interferometer", Nature Materials 7.2, Jan. 13, 2008, pp. 134-137.

Yaroshenko A. et al., "Pulmonary Emphysema Diagnosis with a Preclinical Small-Animal X-Ray Dark-Field Scatter-Contrast Scanner." Radiology, vol. 269, No. 2, Nov. 2013, pp. 427-433.

\* cited by examiner

APPARATUS FOR PRESENTATION OF DARK FIELD X-RAY IMAGE INFORMATION

FIELD OF THE INVENTION

The present invention relates to an apparatus for presentation of dark field X-ray image information, to a system for presentation of dark field X-ray image information, and to a method for presentation of dark field X-ray image information, as well as to a computer program element and a computer readable medium.

BACKGROUND OF THE INVENTION

X-ray dark field radiography is a promising technology for the detection of pulmonary disorders. However, it is unclear how this new information should be presented to the radiologist/doctor in order for a quick and reliable diagnosis, without significantly increasing the time spent per patient.

WO 2017/055527A1 describes that a biomarker of lung condition can conventionally be obtained using a spirometer. A spirometer provides an estimate of the volume of air expelled by the lungs. This is a rather indirect biomarker of the staging of a lung condition, because a reduction in lung volume may only manifest itself at a point where symptoms are well advanced. A lung condition such as Chronic Obstructive Pulmonary Disorder (COPD) is typically not visible on conventional X-ray attenuation images, because the relevant tissue (alveoli-bearing microstructured lung tissue) contains a lot of air. The X-ray dark-field can successfully indicate microstructure, such as lung alveoli. Therefore, imaging the lungs using the dark-field can provide information on the status of COPD.

WO 2009/150565A2 describes that a diagnostic imaging device includes detector elements for detecting gamma-rays indicative of nuclear decay events. Pairs of concurrently detected gamma-rays define lines of response (LORs) which are collected, time stamped, and compiled in list-mode. In tissue perfusion studies, it is beneficial to use the data that concurrently maximizes contrast and signal-to-noise ratio in the reconstructed images. Using the list-mode data, events in an adjustable temporal window are reconstructed and the reconstructed images are analyzed to determine a figure of merit based on contrast and signal-to-noise properties of the image. By iteratively adjusting the temporal window, extending its start point backwards in time, and repeating the reconstructing, analyzing, and adjusting steps, an image with an optimal figure of merit is obtained.

WO 2006/116700A2 relates to a computer-implemented quality assurance system, which includes the steps of retrieving quality assurance and supporting information from a database; receiving information on technical variables from monitoring of the patient, and on radiographic equipment in the performance of an imaging study; generating a quality assurance score after said imaging study based on said technical variables and said quality assurance and supporting information; and performing a quality assurance analysis of the imaging study based on the quality assurance score. The score can be used to perform trending analysis, and provide recommendations for education, and feedback, to clinicians, radiologists, and departments.

SUMMARY OF THE INVENTION

Therefore, it would be advantageous to have an improved technology for providing dark field X-ray image information to a radiologist/doctor.

The object of the present invention is solved with the subject matter of the independent claims, wherein further embodiments are incorporated in the dependent claims. It should be noted that the following described aspects of the invention apply also for the apparatus for presentation of dark field X-ray image information, system for presentation of dark field X-ray image information, and the method for presentation of dark field X-ray image information, and for the computer program element and the computer readable medium.

According to a first aspect, there is provided an apparatus for presentation of dark field information, comprising:

an input unit;
a processing unit; and
an output unit.

The input unit is configured to provide the processing unit with an X-ray attenuation image of a region of interest of an object. The input unit is configured also to provide the processing unit with a dark field X-ray image of the region of interest of the object. The processing unit is configured to define a plurality of sub-regions of the region of interest based on the X-ray attenuation image of the region of interest or based on the dark field X-ray image of the region of interest. The processing unit is configured also to derive at least one quantitative value for each of the plurality of sub-regions, wherein the at least one quantitative value for a sub-region comprises data derived from the X-ray attenuation image of the sub-region and data derived from the dark field X-ray image of the sub-region. The processing unit is configured also to assign a plurality of figures of merit to the plurality of sub-regions, wherein a figure of merit for a sub-region is based on the at least one quantitative value for the sub-region. The output unit is configured to output data representative of the region of interest with figures of merit for the respective sub-regions.

In this way a radiologist is provided with a summary of quantitative information behind the dark field imaging technology with an improved workflow. Sub-regions of a region of a body, such as different parts of a lung, are provided with figures of merit enabling the radiologist to determine if a part of the lung is deviating from what is normal, enabling for example pulmonary disorders to be quickly diagnosed.

In an example, the at least one quantitative value for the sub-region comprises a normalization of the data derived from the X-ray attenuation image of the sub-region with respect to the data derived from the dark field X-ray image of the sub-region.

In this way, the normalized dark field signal can be summarized for the corresponding sub-regions providing an efficient and effective manner in which figures of merit can be provided to the radiologist from which a diagnosis can be made.

In this manner, the effect of the X-rays having passed through a length of the object can be cancelled out, resulting in the least one quantitative value representing a "material constant" for the sub-region of the object and thereby the at least one quantitative value can better be used to determine a deviation from normal, that is not dependent upon the size of the object and/or the size of a patient for example.

In an example, derivation of the at least one quantitative value for the sub-region comprises a combination of data derived from the dark field X-ray image of the sub-region and a 3D model of the sub-region derived from the X-ray attenuation image of the region of interest.

In an example, the data derived from the X-ray attenuation image of the sub-region comprises at least one transmission value of the sub-region and the data derived from the dark field X-ray image of the sub-region comprises at least one dark field value of the sub-region.

In an example, the data derived from the X-ray attenuation image of the sub-region comprises at least one logarithm of the at least one transmission value of the sub-region.

In this way, the data derived from the X-ray attenuation image provides information relating to the attenuation parameter combined with a length through the object.

In an example, the data derived from the X-ray attenuation image of the sub-region comprises a logarithm of a transmission value at a first position of the sub-region subtracted from a logarithm of a transmission value at a second position of the sub-region.

In this way, the effects of beam hardening and Compton scatter can be mitigated.

In an example the data derived from the dark field X-ray image of the sub-region comprises at least one logarithm of the at least one dark field value of the sub-region.

In this way, the data derived from the dark field X-ray image provides information relating to the scattering parameter combined with a length through the object.

In an example, the data derived from the dark field X-ray image of the sub-region comprises a logarithm of a dark field value at a first position of the sub-region subtracted from a logarithm of a dark field value at a second position of the sub-region.

In this manner, the effects of beam hardening and Compton scatter can be mitigated, especially when the corresponding transmission values from the X-ray attenuation image are used at the corresponding two positions from which the data derived from the X-ray attenuation image comprises a logarithm of a transmission value at the first position of the sub-region subtracted from a logarithm of a transmission value at the second position of the sub-region.

In an example, the data derived from the X-ray attenuation image of the sub-region comprises a lung volume of the sub-region determined from at least two transmission values of the sub-region.

In this manner, dark field signals can be normalized to the lung volume, and also lung volume data can be presented to the radiologist along with the normalized dark field signal to better enable a diagnosis to be made.

In an example, the at least one quantitative value for a sub-region is a plurality of quantitative values, and wherein the figure of merit for the sub-region comprises a determination of the homogeneity of the plurality of quantitative values.

According to a second aspect, there is provided a system for presentation of dark field information, the system comprising:
- at least one image acquisition unit; and
- an apparatus for presentation of dark field information according to the first aspect.

The at least one image acquisition unit is configured to provide the X-ray attenuation image, and to provide the dark field X-ray image. The output unit is configured to output the X-ray attenuation image and/or the dark field X-ray image along with the figures of merit for the respective sub-regions of the region of interest According to a third aspect, there is provided a method for presentation of dark field information, comprising:
a) providing an X-ray attenuation image of a region of interest of an object;
b) providing a dark field X-ray image of the region of interest of the object;
c) defining a plurality of sub-regions of the region of interest based on the X-ray attenuation image of the region of interest or based on the dark field X-ray image of the region of interest;
d) deriving at least one quantitative value for each of the plurality of sub-regions, wherein the at least one quantitative value for a sub-region comprises data derived from the X-ray attenuation image of the sub-region and data derived from the dark field X-ray image of the sub-region;
e) assigning a plurality of figures of merit to the plurality of sub-regions, wherein a figure of merit for a sub-region is based on the at least one quantitative value for the sub-region; and
f) outputting data representative of the region of interest with figures of merit for the respective sub-regions.

In an example, step d) comprises normalizing the data derived from the X-ray attenuation image of the sub-region with respect to the data derived from the dark field X-ray image of the sub-region.

According to another aspect, there is provided a computer program element controlling apparatus as previously described which, in the computer program element is executed by processing unit, is adapted to perform the method steps as previously described. According to another aspect, there is provided a computer readable medium having stored computer element as previously described.

Advantageously, the benefits provided by any of the above aspects and examples equally apply to all of the other aspects and examples and vice versa.

The above aspects and examples will become apparent from and be elucidated with reference to the embodiments described hereinafter.

BRIEF DESCRIPTION OF THE DRAWINGS

Exemplary embodiments will be described in the following with reference to the following drawings.

DETAILED DESCRIPTION OF EMBODIMENTS

Figure 1:
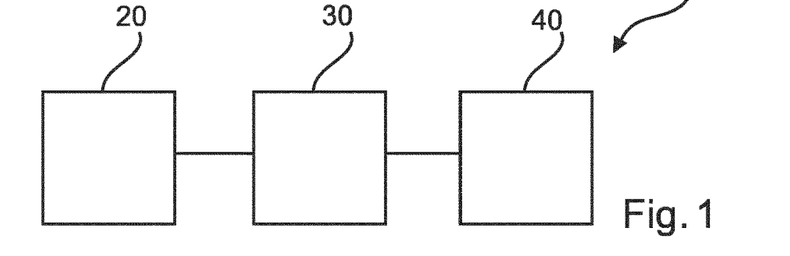
FIG. 1 shows an example of an apparatus for presentation of dark field X-ray image information.

FIG. 1 shows an example of an apparatus 10 for presentation of dark field information. The apparatus 10 comprises an input unit 20, a processing unit 30, and an output unit 40. The input unit 20 is configured to provide the processing unit 30 with an X-ray attenuation image of a region of interest of an object. The input unit 20 is configured also to provide the processing unit 30 with a dark field X-ray image of the region of interest of the object. The processing unit 30 is configured to define a plurality of sub-regions of the region of interest based on the X-ray attenuation image of the region of interest or based on the dark field X-ray image of the region of interest. The processing unit 30 is configured also to derive at least one quantitative value for each of the plurality of sub-regions. The at least one quantitative value for a sub-region comprises data derived from the X-ray attenuation image of the sub-region and data derived from the dark field X-ray image of the sub-region. The processing unit 30 is configured also to assign a plurality of figures of merit to the plurality of sub-regions. A figure of merit for a sub-region is based on the at least one quantitative value for the sub-region. The output unit 40 is configured to output data representative of the region of interest with figures of merit for the respective sub-regions.

In an example, the region of interest is a lung.

In an example, the plurality of sub-regions are defined through a segmentation of the region of the object. For example, the segmentation can be oriented on anatomical structures and also on manually defined regions.

According to an example, the at least one quantitative value for the sub-region comprises a normalization of the data derived from the X-ray attenuation image of the sub-region with respect to the data derived from the dark field X-ray image of the sub-region.

According to an example, derivation of the at least one quantitative value for the sub-region comprises a combination of data derived from the dark field X-ray image of the sub-region and a 3D model of the sub-region derived from the X-ray attenuation image of the region of interest.

According to an example, the data derived from the X-ray attenuation image of the sub-region comprises at least one transmission value of the sub-region and the data derived from the dark field X-ray image of the sub-region comprises at least one dark field value of the sub-region.

According to an example, the data derived from the X-ray attenuation image of the sub-region comprises at least one logarithm of the at least one transmission value of the sub-region.

According to an example, the data derived from the X-ray attenuation image of the sub-region comprises a logarithm of a transmission value at a first position of the sub-region subtracted from a logarithm of a transmission value at a second position of the sub-region.

According to an example, the data derived from the dark field X-ray image of the sub-region comprises at least one logarithm of the at least one dark field value of the sub-region.

According to an example, the data derived from the dark field X-ray image of the sub-region comprises a logarithm of a dark field value at a first position of the sub-region subtracted from a logarithm of a dark field value at a second position of the sub-region. According to an example, the data derived from the X-ray attenuation image of the sub-region comprises a lung volume of the sub-region determined from at least two transmission values of the sub-region.

According to an example, the at least one quantitative value for a sub-region is a plurality of quantitative values. The figure of merit for the sub-region can then comprise a determination of the homogeneity of the plurality of quantitative values.

Figure 2:
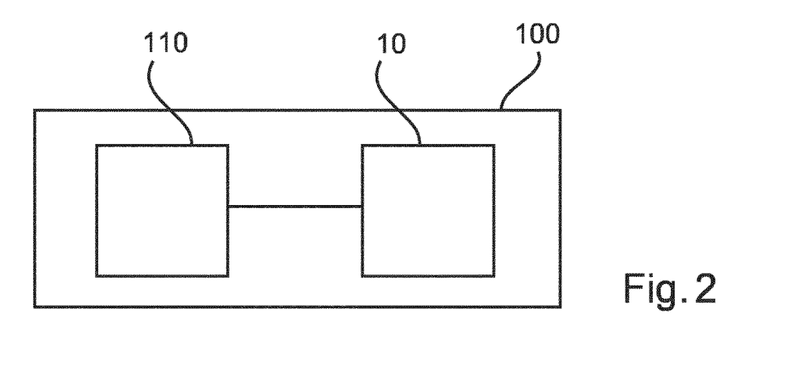
FIG. 2 shows an example of a system for presentation of dark field X-ray image information.

FIG. 2 shows an example of a system 100 for presentation of dark field information. The system 100 comprises at least one image acquisition unit 110, and an apparatus 10 for presentation of dark field information as described with respect to FIG. 1 and any of the described examples or combination of examples. The at least one image acquisition unit 110 is configured to provide the X-ray attenuation image, and to provide the dark field X-ray image. The output unit 40 is configured to output the X-ray attenuation image and/or the dark field X-ray image along with the figures of merit for the respective sub-regions of the region of interest.

In an example, the at least one image acquisition unit comprises a grating based dark field X-ray imaging device. In an example, the at least one image acquisition unit comprises an interferometer arrangement.

In an example, the at least one image acquisition unit comprises an X-ray imaging device. For example, the device can be a radiography system prepared for Dark Field imaging.

In an example, the at least one image acquisition unit can operate in a standard radiography mode, with transmitted intensities of radiation providing information on attenuation through the object. In an example, the same image acquisition unit can be used to acquire the attenuation and dark field images. For example, the attenuation and dark field information can be the output of the evaluation of the same acquisition data. This data can be multiple exposures (for example between 4 and 20) showing the image with different phase positions of one of the gratings. A full field system can be implemented with gratings as large as the detector.

In an example, the at least one image acquisition unit generates an attenuation image, relating to the detection of intensity values of X-rays with and without the object in the examination region. In an example, the at least one image acquisition unit generates a dark field (or de-coherence) image, relating to the detection of fringe visibilities of the X-rays with and without the object in the examination region. In an example, the at least one image acquisition unit generates any combination of these images. For example, the at least one image acquisition unit can generate an attenuation image, and generate a dark field image. In an example, an attenuation image and a dark field image can be generated at the same time.

In an example, the object is a body or body part and the region is a lung of the body. In an example, the region can be other parts of the body.

Figure 3:
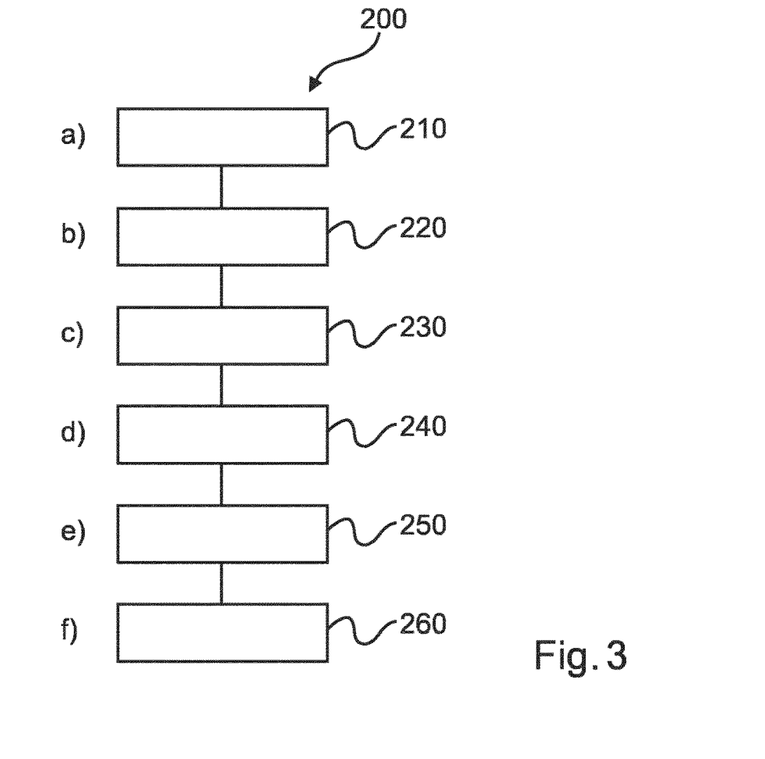
FIG. 3 shows an example of a method for presentation of dark field X-ray image information.

FIG. 3 shows a method 200 for presentation of dark field information in its basic steps. The method 200 comprises:

in a providing step 210, also referred to as step a), providing an X-ray attenuation image of a region of interest of an object;

in a providing step 220, also referred to as step b), providing a dark field X-ray image of the region of interest of the object; in a defining step 230, also referred to as step c), defining a plurality of sub-regions of the region of interest based on the X-ray attenuation image of the region of interest or based on the dark field X-ray image of the region of interest;

in a deriving step 240, also referred to as step d), deriving at least one quantitative value for each of the plurality of sub-regions, wherein the at least one quantitative value for a sub-region comprises data derived from the X-ray attenuation image of the sub-region and data derived from the dark field X-ray image of the sub-region;

in an assigning step 250, also referred to as step e), assigning a plurality of figures of merit to the plurality of sub-regions, wherein a figure of merit for a sub-region is based on the at least one quantitative value for the sub-region; and in an outputting step 260, also referred to as step f), outputting data representative of the region of interest with figures of merit for the respective sub-regions.

According to an example, step d) comprises normalizing the data derived from the X-ray attenuation image of the sub-region with respect to the data derived from the dark field X-ray image of the sub-region.

In an example, step d) comprises combining data derived from the dark field X-ray image of the sub-region and a 3D model of the sub-region derived from the X-ray attenuation image of the region of interest.

In an example, the data derived from the X-ray attenuation image of the sub-region comprises at least one transmission value of the sub-region and the data derived from the dark field X-ray image of the sub-region comprises at least one dark field value of the sub-region.

In an example, the data derived from the X-ray attenuation image of the sub-region comprises at least one logarithm of the at least one transmission value of the sub-region.

In an example, the data derived from the X-ray attenuation image of the sub-region comprises a logarithm of a transmission value at a first position of the sub-region subtracted from a logarithm of a transmission value at a second position of the sub-region.

In an example, the data derived from the dark field X-ray image of the sub-region comprises at least one logarithm of the at least one dark field value of the sub-region.

In an example, the data derived from the dark field X-ray image of the sub-region comprises a logarithm of a dark field value at a first position of the sub-region subtracted from a logarithm of a dark field value at a second position of the sub-region.

In an example, the data derived from the X-ray attenuation image of the sub-region comprises a lung volume of the sub-region determined from at least two transmission values of the sub-region.

In an example, the at least one quantitative value for a sub-region is a plurality of quantitative values, and wherein the figure of merit for the sub-region comprises a determination of the homogeneity of the plurality of quantitative values.

The apparatus, system and method for presentation of dark field X-ray image information is now described in further detail with reference to FIGS. 4-5.

Figure 4:
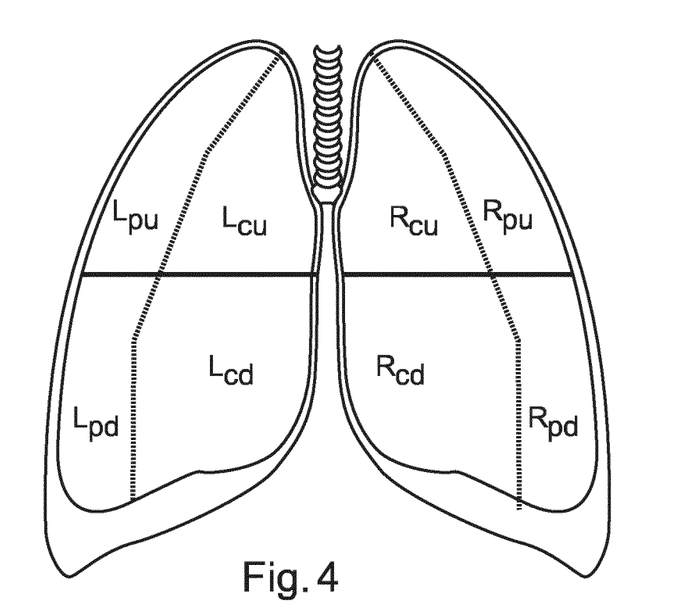
FIG. 4 shows two examples of how imagery of a lung can be split or segmented into sub-regions.

FIG. 4 shows two examples of how the sub-regions of the region are defined, for the example of defining sub-regions of a lung. The lung has been split up into different segments based on the conventional X-ray chest radiogram, also termed the X-ray attenuation image. The segmentation can be oriented both on anatomical structures but also on manually defined regions. At the top of FIG. 4, the lung is split, or segmented, into lobes. At the bottom of FIG. 4, the lung is split into geometrical sub-regions and in this example has been split into 4 sub-regions, but could have been split into 2-9 sub-regions as required. The X-ray attenuation image or the dark field image can be split or segmented in order to define the sub-regions, thus rather than an attenuation image of the lung being split up into different segments a dark field image of the lung could have been split up in a similar manner into different segments.

Based on the defined sub-regions of the lung, local quantitative information on the quality of the lung based on the combination of the dark-field and transmission signals is derived. This is achieved through the normalization of the dark-field signal. Then the normalized dark field is summarized for the corresponding sub-region, using for example a 0-4 scale, as described below in the table:

| Value S | Signal strength |
|---|---|
| 4 | Maximum dark field signal (based on previous experience) |
| 3 | Slightly decreased dark field signal (deviation to maximum case of 15%) |
| 2 | Significantly decreased dark field signal (deviation to maximum case of 30%) |
| 1 | Very significant decrease in dark field signal (deviation to maximum case of 45%) |
| 0 | More than 45% dark field signal decrease up to NO visible Dark Field signal |

Figure 5:
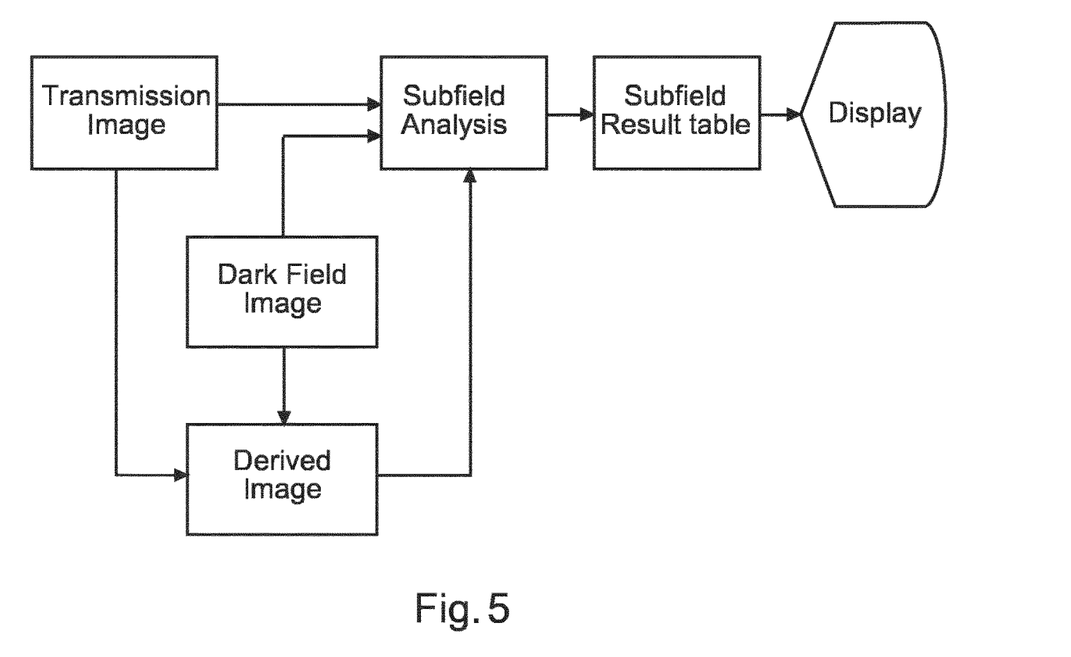
FIG. 5 shows a detailed workflow of an example of operation of a system for presentation of dark field X-ray image information.

The following provides more details regarding the dark field normalization, with a specific example of the dark field signal being normalized with respect to the transmission of the X-ray attenuation image, however the dark field image can be normalized with respect to the lung volume for example, with a detailed workflow shown in FIG. 5.

Starting with the X-ray attenuation image, the following applies:

I=Intensity of X-ray; $I_0$=the un-attenuated intensity
µ=attenuation parameter
l=length through the material
T=Transmission; $T=I/I_0$ $I=I_0 e^{-\mu l}$
$T=e^{-\mu l}$ The negative logarithmical transmission is therefore closely related to the object properties:

$-\ln(T)=\mu l$

Thus, the negative logarithm of transmission is equal to the dimension of the object convolved with the attenuation parameter for the object material at that position.

Then considering the dark field signal, the following applies:

V=Visibility of fringe pattern in interferometer; $V_0$=the un-attenuated visibility
ε=scatter parameter
l=length through the material
D=Dark Field; $D=V/V_0$ $V=V_0 e^{-\varepsilon l}$
$D=e^{-\varepsilon l}$ The negative logarithmical of the Dark Field is then relevant to the object properties as well:

$-\ln(D)=\varepsilon l$

Thus the negative logarithm of the dark field signal is equal to the dimension of the object convolved with the scatter parameter of the object at this point. The value "εl" can also be termed the dark field signal.

The particular advantages of dark field imaging for the lungs is that the lungs have an ε>0, which is opposite to most other tissues. The highest fringe signal achieved is when the object is not present, and the visibility of the interferometer is $V_0$. In the log domain, $-\ln(D=1)=0$, and when there is no object the dark field signal of "no object" has a value of 0. With a lung present the visibility deteriorates, and $-\ln(D)>0$. Thus the presence of the lungs generates a dark field signal with dark field signal $=-\ln(D)$: dark field signal=εl.

It is to be noted that healthy lung tissue has been found to have high values for ε and pathologic lungs low values for ε.

Regarding normalization, if there was only lung tissue involved in imaging, and no other soft tissue, no bones and no air cavities, the two exponential laws would lead to similar results.

$-\ln(T)=\mu l$ $-\ln(D)=\varepsilon l$=dark field signal

The images T(x,y) and D(x,y) would both represent the dimensions of the object l(x,y).

However, by normalizing the dark field signal with respect to the transmission in the attenuation image, in the logarithmic domain, and where "normalization" also applies in the reciprocal, the ratio becomes:

$$\frac{\ln(T)}{\ln(D)} = \mu/\varepsilon$$

Thus, by determining the ratio of the two images through such a normalization, the impact of the length through the object at a position l(x,y) cancels out. The quotient µ/ε can then be considered to be a "material constant" for this very lung.

In this way, through a normalization of the dark field signal in this manner, the effect of the size of the object can be mitigated. Thus, a low dark field-signal can represent a pathological lung, but can also be due to dark field imaging of a lung with a small dimension "l". However, by normalizing the dark field signal, material constant information for the lung can be determined that is de-convoled from the length through the lung, enabling healthy lung tissue to be differentiated from pathological tissue.

However, in reality the "dark field signal-value" is not zero outside the lungs. The reasons are beam hardening and Compton scatter, which both lead to decreasing fringe visibility and as such to a "fake dark field Signal" or false dark field signal.

To account for this, and take this out of the normalization, specific corrections or local references can be applied. This leads to a normalization based on a dark field signal at two locations (1 and 2) in the lung being used in combination with the transmission value at the two locations in the lung, such that:

$$\frac{\ln(T_1) - \ln(T_2)}{\ln(D_1) - \ln(D_2)} = \mu/\varepsilon$$

The above relates to one example of how the dark field signal can be normalized with respect to the transmission "signal". However, the dark field signal can be normalized with respect to the lung volume, which is itself derived from the transmission signal. This is possible because it is possible to convert the T-signal into mm of air within the thorax. With additional 2-d-information T(x,y), one can associate each lung with a lung volume in mm³. Further details relating to determination of a lung volume in this manner can be found in US2016/0210739A1.

Each sub-region then has a signal strengths shown as summarized values in the above table, where there are actually a number of different signal strengths for each sub-region. However, to provide the radiologist with further information in addition to the signal strength for a sub-region, the homogeneity of the signal for a sub-region is also to be provided to the radiologist, and a value H assigned between 0 and 3.

| Value H | Homogeneity |
|---|---|
| 0 | The signal is homogeneous |
| 1 | Signal deviation within two neighboring signal values (e.g. it is not clear whether the signal strength should be 4 or 3) |

-continued

| Value H | Homogeneity |
|---|---|
| 2 | Signal deviation within three signal values |
| 3 | (e.g. it is not clear whether the signal strength should be 4 or 2) |

Thus, as the result of the presented apparatus, system and method, the radiologist will have a conventional x-ray chest radiography displayed and a table displaying the normalized dark-field values for the different sub-regions, as well as the signal homogeneity and the corresponding lung volumes. This information helps the radiologist make an effective diagnosis.

As the length of a projection ray traversing through the lung part of the overall thorax cannot be measured directly from the 2D dark field image, the absolute signal magnitude is not determined. This can be addressed through normalization. However, the projective nature of the 2D DAX image leads to the fact that for many locations two or more lobes/segments/sub-regions are superimposed onto each other, so that the lobe-wise contribution is not determined. Therefore, rather that normalizing the dark field signal with respect to the transmission "signal" in the manner as discussed above, a 2D dark field projection image can be combined with a lung lobe 3D model in order to enable quantitative values for the sub-region to be determined.

The lung lobe model can either be:
(a) generic and adapted to the lung contours in the absorption image accompanying the dark field image, or
(b) patient-specific and adapted to an additional 3D CT image of the patient, and subsequently adapted to the lung contours in the absorption image accompanying the dark field image, to account for possibly different inspiration state between the CT and dark field examinations.

Using the assumption that the dark field signal is homogeneous within one lobe (or segment), an overdetermined system of linear equations is solved for K unknowns (5 lobes or 20 segments). Then taking N projection rays, an equation is formed for each of the N projection rays (N>>K). For each equation, the model is used to determine a partial ray length for each of the lobes (segments) through which the ray traverses. The unknowns are the mean DAX signal per volume-element, which are solved for by a standard linear equation solver under the constraint of non-negative solutions. The sum of which should yield the observed dark field projection value. In this manner, complementary information from a 2D dark field image and a lung lobe model derived from an X-ray attenuation image is used to enable lobar values to be determined, when the alveoli are not visible in the CT image, and the lobar boundaries are not visible in the dark field image. The K lobar (segmental) dark signals can be reported as numerical results to the radiologist, and optionally translated into a coronal/sagittal graphic using e.g. a heat map pseudo color scale. Reporting for each lobe/segment can be both the mean signal per volume-element, and the lobe-cumulative signal value.

This is explained in more detail with reference to FIGS. 6-8.

Figure 6:
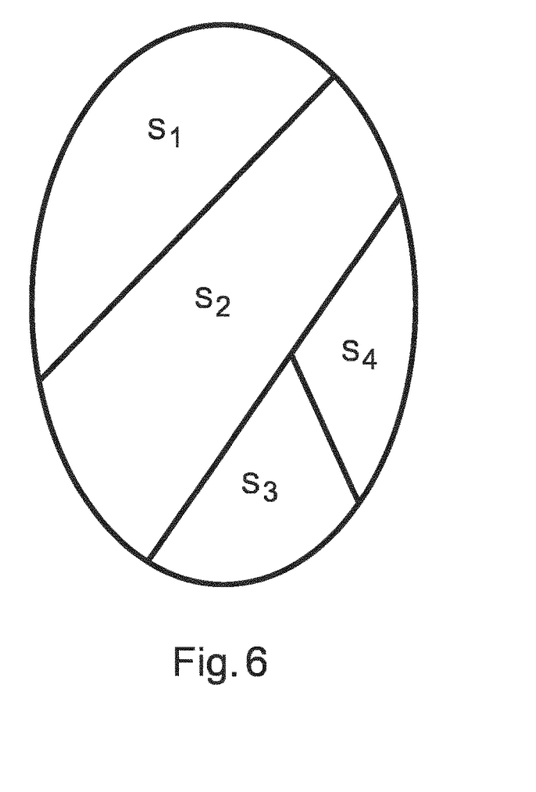
FIG. 6 shows a 3D shape of the lung with lung segments.

FIG. 6 shows a 3D shape of the lung with lung segments.

The segmentation and model adaption, as discussed at a) or b) above, provides the 3D shape of the lung including an estimate for the location and boundaries of the individual lung segments. These are labeled S1 to S4 in FIG. 6.

Figure 7:
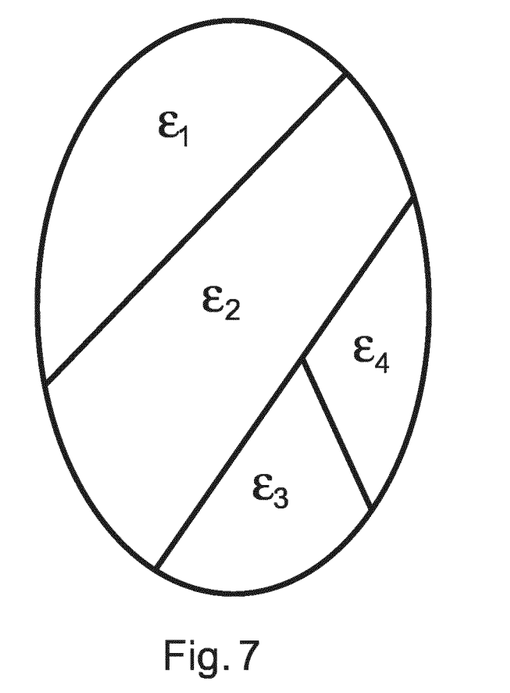
FIG. 7 shows the 3D shape of the lung with scatter properties.

FIG. 7 shows the 3D shape of the lung with scatter properties. Each segment is assumed to have a homogeneous scatter property, denoted as $\varepsilon_1$ to $\varepsilon_4$.

Figure 8:
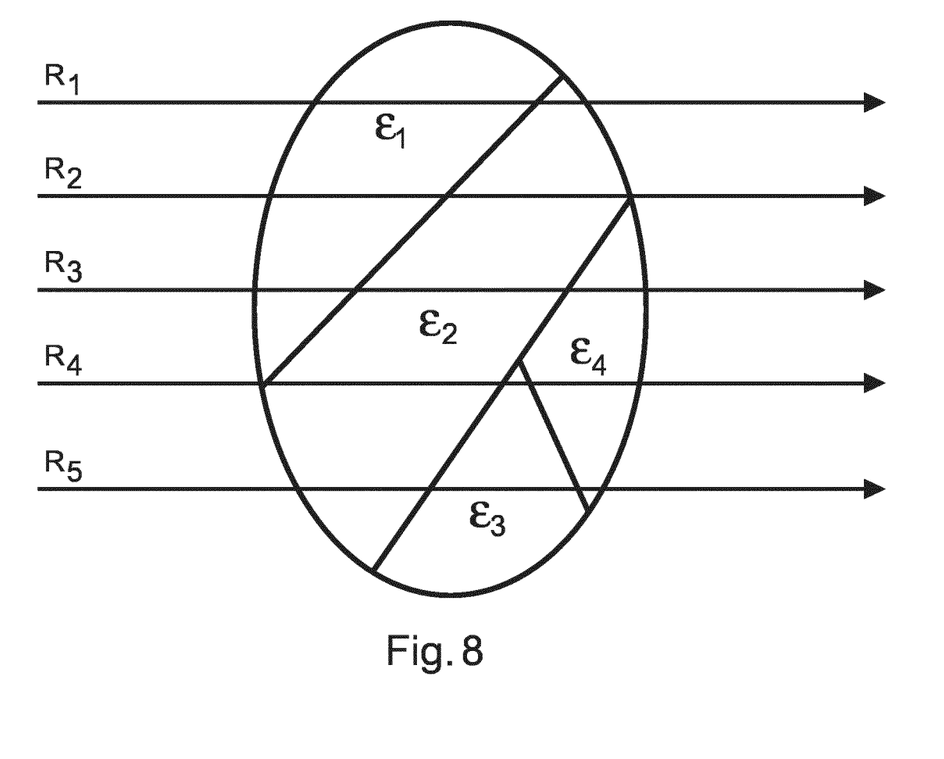
FIG. 8 shows X-ray projection rays associated with the 3D shape of the lung.

FIG. 8 shows X-ray projection rays associated with the 3D shape of the lung. The projection geometry is also known, i.e. for each measurement on the detector, it is known in 3D, which route an X-ray took through the lung. Consequently, for each ray $R_1$ to $R_5$, it is known how long the path length through each lung segment was. Let the path length of ray i through segment j be denoted by $L_{ij}$.

The expected DAX (dark field) signal accumulated in ray i (i.e. the DAX signal at the detector pixel where the ray i hits the detector) is in this model $$D_i = \sum_j L_{ij}\varepsilon_j$$

In matrix-vector notation, this is represented as $$\vec{D} = L\vec{\varepsilon}$$

Usually, there are thousands of rays but only 20 lung segments. Thus, this linear system of equations is heavily overdetermined. Thus a stable solution can be obtained for instance using the Moore-Penrose pseudo-inverse $L^{554}$, which can be computed as $$L^\dagger = (L^T L)^{-1} L^T$$

$$\vec{\varepsilon} = (L^T L)^{-1} L^T \vec{D}$$

Further details on x-ray dark field imaging can be found in the following papers: Pfeiffer, Franz, et al. "Hard-X-ray dark-field imaging using a grating interferometer." Nature materials 7.2 (2008), pages 134-137; and Yaroshenko, Andre, et al. "Pulmonary emphysema diagnosis with a preclinical small-animal x-ray dark-field scatter-contrast scanner." Radiology 269.2 (2013), pages 427-433.

In another exemplary embodiment, a computer program or computer program element is provided that is characterized by being configured to execute the method steps of the method according to one of the preceding embodiments, on an appropriate system.

The computer program element might therefore be stored on a computer unit, which might also be part of an embodiment. This computing unit may be configured to perform or induce performing of the steps of the method described above. Moreover, it may be configured to operate the components of the above described apparatus. The computing unit can be configured to operate automatically and/or to execute the orders of a user. A computer program may be loaded into a working memory of a data processor. The data processor may thus be equipped to carry out the method according to one of the preceding embodiments.

This exemplary embodiment of the invention covers both, a computer program that right from the beginning uses the invention and computer program that by means of an update turns an existing program into a program that uses the invention.

Further on, the computer program element might be able to provide all necessary steps to fulfill the procedure of an exemplary embodiment of the method as described above.

According to a further exemplary embodiment of the present invention, a computer readable medium, such as a CD-ROM, is presented wherein the computer readable medium has a computer program element stored on it which computer program element is described by the preceding section.

A computer program may be stored and/or distributed on a suitable medium, such as an optical storage medium or a solid state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfill the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. A computer-implemented apparatus for presentation of dark field information, comprising:
   a processing circuitry;
   a memory containing instructions that, when executed by the processing circuitry, configure the apparatus to:
   provide an X-ray attenuation image and a dark field X-ray image of a region of interest of an object;
   define a plurality of sub-regions of the region of interest based on the X-ray attenuation image of the region of interest or based on the dark field X-ray image of the region of interest;
   derive at least one quantitative value for each of the plurality of sub-regions, wherein the at least one quantitative value for a sub-region comprises data derived from the X-ray attenuation image of the sub-region and data derived from the dark field X-ray image of the sub-region;

assign a plurality of figures of merit to the plurality of sub-regions, wherein a figure of merit for a sub-region is based on the at least one quantitative value for the sub-region; and output data representative of the region of interest with figures of merit for the respective sub-regions.

2. The apparatus according to claim 1, wherein the at least one quantitative value for the sub-region comprises a normalization of the data derived from the X-ray attenuation image of the sub-region with respect to the data derived from the dark field X-ray image of the sub-region.

3. The apparatus according to claim 1, further comprising combining data derived from the dark field X-ray image of the sub-region and a 3D model of the sub-region derived from the X-ray attenuation image of the region of interest.

4. The apparatus according to claim 1, wherein the data derived from the X-ray attenuation image of the sub-region comprises at least one transmission value of the sub-region and the data derived from the dark field X-ray image of the sub-region comprises at least one dark field value of the sub-region.

5. The apparatus according to claim 4, wherein the data derived from the X-ray attenuation image of the sub-region comprises at least one logarithm of the at least one transmission value of the sub-region.

6. The apparatus according to claim 5, wherein the data derived from the X-ray attenuation image of the sub-region comprises a logarithm of a transmission value at a first position of the sub-region subtracted from a logarithm of a transmission value at a second position of the sub-region.

7. The apparatus according to claim 4, wherein the data derived from the dark field X-ray image of the sub-region comprises at least one logarithm of the at least one dark field value of the sub-region.

8. The apparatus according to claim 7, wherein the data derived from the dark field X-ray image of the sub-region comprises a logarithm of a dark field value at a first position of the sub-region subtracted from a logarithm of a dark field value at a second position of the sub-region.

9. The apparatus according to claim 4, wherein the data derived from the X-ray attenuation image of the sub-region comprises a lung volume of the sub-region determined from at least two transmission values of the sub-region.

10. The apparatus according to claims 1, wherein the figure of merit for the sub-region comprises a determination of homogeneity of the plurality of quantitative values.

11. A computer-implemented method for presenting dark field information, comprising:

providing an X-ray attenuation image of a region of interest of an object;

providing a dark field X-ray image of the region of interest of the object;

defining a plurality of sub-regions of the region of interest based on the X-ray attenuation image of the region of interest or based on the dark field X-ray image of the region of interest;

deriving at least one quantitative value for each of the plurality of sub-regions, wherein the at least one quantitative value for a sub-region comprises data derived from the X-ray attenuation image of the sub-region and data derived from the dark field X-ray image of the sub-region;

assigning a plurality of figures of merit to the plurality of sub-regions, wherein a figure of merit for a sub-region is based on the at least one quantitative value for the sub-region; and outputting data representative of the region of interest with figures of merit for the respective sub-regions.

12. The method according to claim 11, further comprising normalizing the data derived from the X-ray attenuation image of the sub-region with respect to the data derived from the dark field X-ray image of the sub-region.

13. A non-transitory computer-readable medium having executable instructions stored thereon which, when executed by at least one processor, cause the at least one processor to perform a method for presenting dark field information, comprising:

providing an X-ray attenuation image of a region of interest of an object;

providing a dark field X-ray image of the region of interest of the object;

defining a plurality of sub-regions of the region of interest based on the X-ray attenuation image of the region of interest or based on the dark field X-ray image of the region of interest;

deriving at least one quantitative value for each of the plurality of sub-regions, wherein the at least one quantitative value for a sub-region comprises data derived from the X-ray attenuation image of the sub-region and data derived from the dark field X-ray image of the sub-region;

assigning a plurality of figures of merit to the plurality of sub-regions, wherein a figure of merit for a sub-region is based on the at least one quantitative value for the sub-region; and outputting data representative of the region of interest with figures of merit for the respective sub-regions.

* * * * *